US006620427B2

(12) United States Patent
Lasekan et al.

(10) Patent No.: US 6,620,427 B2
(45) Date of Patent: Sep. 16, 2003

(54) METHOD FOR IMPROVING BONE MINERALIZATION

(75) Inventors: John B. Lasekan, Worthington, OH (US); Marc L. Masor, Worthington, OH (US); Michael B. Montalto, Upper Arlington, OH (US); John D. Benson, Powell, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/876,022

(22) Filed: Jun. 8, 2001

(65) Prior Publication Data

US 2003/0026860 A1 Feb. 6, 2003

Related U.S. Application Data

(60) Provisional application No. 60/286,140, filed on Apr. 24, 2001, now abandoned.

(51) Int. Cl.$^7$ .............................................. A61K 47/00
(52) U.S. Cl. .................... 424/439; 424/400; 424/600; 426/601
(58) Field of Search ................. 424/400, 439; 426/601

(56) References Cited

U.S. PATENT DOCUMENTS 3,649,295 A * 3/1972 Bernhart ..................... 426/598
4,721,626 A * 1/1988 Rule .......................... 426/601
6,136,858 A   10/2000 Kuchan et al.

OTHER PUBLICATIONS

Webster's New College Dictionary, 1995, p. 697.*
Remington's Pharmaceutical Sciences, 18$^{th}$ Edition, 1990, p. 336.*
Carnielli, et al., "Structural Position and Amount of Palmitic Acid in Infant Formulas: Effect on Fat, Fatty Acid, and Mineral Balance", Journal of Pediatric Gastroenterology and Nutrition, vol. 23, No. 5, 1996, pp. 553–560.
Quinlan, et al., "The Relationship between Stool Hardness and Stool Composition in Breast– and Formula–Fed Infants", Journal of Pediatric Gastroenterology and Nutrition, vol. 20, No. 1, 1995, pp. 81–90.
Specker, et al., "Randomized Trial of Varying Mineral Intake on Total Body Bone Mineral Accretion During the First Year of Life", Pediatrics, vol. 99, No. 6, Jun. 1997.
Kennedy, et al., "Double–blind, randomized trial of a synthetic triacylglycerol in formula–fed term infants: effects on stool biochemistry, stool characteristics, and bone mineralization", Am J Clin Nutr, 1999, 70:920–7.
NIH Consensus Conference, "Optimal Calcium Intake: NIH Consensus Development Panel on Optimal Calcium Intake", JAMA, Dec. 28, 1994, vol. 272, No. 24.
Nelson, et al., "Absorption of Fat and Calcium by Infants Fed a Mill–Based Formula Containing Palm Olein", Journal of the American College of Nutrition, vol. 17, No. 4, 327–332 (1998).
Nelson et al., "Palm olein in infant formula: absorption of fat and minerals by normal infants", Am J Clin Nutr, 1996; 64: 2916.
Motil, "Editorial: Fat and Calcium Absorption in Infancy Revisited", Journal of the American College of Nutrition, vol. 17, No. 4, 303–305 (1998).
Koo, et al., "Bone Mineralization in Healthy Term Infants Fed Milk Protein–Based Formulas With or Without Palm Olein: A Randomized, Double–Blinded Trial", Abstract of Presentation on Apr. 20, 2001.
Hansen, et al., "Impact of Palm Olein (PO) in Infant Feedings on Fat and Calcium (CA) Absorption in Growing Premature Infants", J Amer Coll Nutr, 15: 526, 1996, Abstract 47.
Hansen, et al., "Impact of Palm Olein (PO) in Infant Feedings on Growth in Normal Term Infants", J Amer Coll Nutr, 15: 526, 1996, Abstract 48.
Nur, et al., "Parenteral Chromium Toxicity in Newborns Receiving Parenteral Nutrition", J Amer Coll Nutr, 15: 526, 1996, Abstract 49.
Koo, et al., "Bone Mineralization in Healthy Term Infants Fed Milk Protein–Based Formulas With or Without Palm Olein (PO): A Randomized, Double–Blinded Trial", Abstract, American Pediatric Society Society for Pediatric Research, Monday, Apr. 30, 2001.

* cited by examiner

Primary Examiner—Thurman K. Page
Assistant Examiner—Charesse Evans
(74) Attorney, Agent, or Firm—William J. Winter; Thomas D. Brainard

(57) ABSTRACT

The present invention is directed to a method for increasing the bone mineralization of a human, and more preferably an infant or toddler. The method comprises administering to said human a source of calcium and a fat blend that is low in palmitic acid. The enhanced mineralization results in the production of a higher peak bone mass and correspondingly lowers the incidence of osteoporosis.

9 Claims, No Drawings

METHOD FOR IMPROVING BONE MINERALIZATION

This application is related to a provisional patent application Ser. No. 60/286,140 filed Apr. 24, 2001, now abandoned.

The present invention relates to a method for increasing bone mineralization in a pediatric population. Other aspects of the invention relate to methods for improving the nutritional status of infants and toddlers.

BACKGROUND

Bone serves an important physiologic role. It provides mechanical strength. All of the bones collectively, need to be strong enough to support the entire weight of the body, and any additional mechanical burden. It is widely accepted that bone mineral content and density, are directly correlated with the mechanical strength of the bone.

Bone is composed primarily of matrix proteins and calcium salts. Bone growth involves not only an increase in bone size, but an increase in the amount of such components as well. Bone growth is controlled by osteoblasts. These osteoblasts adhere to the terminal portion of existing bone and secrete bone matrix proteins, which differentiate into bone cells (osteocytes) and become part of the tissue of the bone. These osteoid tissues are then mineralized, primarily by calcium and phosphorus. The mineralization gives the bone its mechanical strength and allows it to serve its physiologic role. Substantial bone growth continues for up to the first 20 years of life.

However, after age 35, bone mass and mineral content begin declining gradually reducing the strength of the bone tissue. Consequently, when mechanical strength declines to a certain level, the individual is at greater risk of bone fracture. This is often referred to as osteoporosis.

Medical research has focused on ways of preventing the occurrence of osteoporosis. This research has shown that one of the most effective means of preventing osteoporosis is the establishment of a high bone mass during the childhood years. The establishment of significant bone mass allows a greater loss of bone before osteoporosis becomes problematic. Investigators have started to study childhood diets and their impact on bone formation. Consumption of calcium is an important dietary variable in promoting the development of substantial bone mass in the individual.

Part of this research has examined what impact, if any, infant formula has on bone development. Nelson et al, Journal of the American College of Nutrition, Vol. 17, No. 4, 327–332 (1998), evaluated whether the fatty acid content of infant formula impacted calcium absorption. Nelson et al determined that oil blends did have an impact on calcium absorption. Nelson et al found that the presence of palm olein oil reduced calcium absorption by approximately 35%, when compared to formula which did not contain palm olein oil. The authors concluded that this reduced calcium absorption was unlikely to have any significant physiologic impact on the infant, including bone mineralization. The authors stated that the most likely adverse effect is constipation in the infant.

Nelson et al also evaluated the impact of palm olein on calcium absorption in a different group of infants Am J Clin Nutr 1996;64:291-6 (1996). The results obtained in this study were consistent with the results described by Nelson et al supra. Infants consuming formula containing palm olein oil had lower rates of calcium absorption. The authors emphasized that the clinical significance of such reduced absorption is unknown.

Motil commented on the work of Nelson et al supra, in the Journal of the American College of Nutrition, Vol. 17, No. 4, 303–305 (1998). Motil reiterated that Nelson et al had documented that infants consuming palm olein oil had lower relative calcium absorption, when compared to a group of infants consuming alternative fats. However Motil emphasized that these findings were insignificant from a clinical standpoint. Motil emphasized that calcium homeostasis is a highly regulated process and is not dependent solely upon the amount of calcium that is absorbed. Further, infants in the palm olein group were receiving 100 mg/day of calcium, which is the established RDA. Thus, a fair reading of Motil is that the presence of palm olein is expected to have no impact upon the rate of bone mass development in an infant.

Kennedy et al evaluated an infant formula which contained a synthetic triglyceride (STG) Am J Clin Nutr 1999:70:920-7. This STG contained palmitic acid in the sn-2 position of the glycerol nucleus (i.e. the center carbon atom). This STG is structurally similar to the triglyceride contained in human breast milk. An infant formula containing this STG was compared against a formula containing triglycerides, in which the palmitic acid was contained primarily in the 1- and 3-positions of the glycerol nucleus. These triglycerides are typically contained in infant formula and are obtained from vegetable oils. Kennedy et al evaluated growth rates, fat absorption, and bone mineralization of the two groups. Similar parameters were observed in a group of infants consuming breast milk. Kennedy found that infants consuming the STG had rates of bone mineralization comparable to the breast fed group. Infants receiving the triglycerides obtained from vegetable oils had lower rates of bone mineralization than infants consuming the STG.

Kennedy noted that enhanced calcium absorption had previously been observed with formulae having reduced palmitate content. However, the fatty acid profile of such formula differs substantially from that of breast milk and therefore caution should exercised in its consumption. Kennedy emphasized that palmitic acid is the predominant fatty acid in human milk and the clinical significance of omitting this fatty acid needs further study.

Thus while the prior art clearly establishes that palmitic acid frombovine and vegetable sources negatively impacts the absorption of calcium, the clinical significance of this finding is unknown. Numerous authors agree that the impact of this finding on bone mass is unknown, but probably is clinically insignificant. Other authors suggest caution in the utilization of low palmitic acid formula since it's fatty acid profile differs so significantly from human milk.

SUMMARY OF THE INVENTION

In accordance with the present invention, it has been discovered that it is possible to enhance bone mass accretion in an infant or toddler. This increased bone mass can be accomplished by enterally feeding the juvenile a formula containing a source of calcium and a source of fat, in which the fatty acid profile is characterized by having a palmitic acid content of about 19 w/w %, or less. Such a feeding regimen will result in an enhanced rate of bone mineralization and ultimately enhanced skeletal strength.

The pediatric formula utilized in the method of the present invention will typically be an infant formula. It should contain sufficient nutrients to promote the growth and development of the juvenile. It typically will contain protein, carbohydrate, vitamins, and minerals, as is known in the art. The formula will contain calcium as is known in the art. The key to the invention is the utilization of a fat blend that is low in palmitic acid. While the prior art demonstrates that palmitic acid interferes with the absorption of calcium, the enclosed human clinical studies demonstrate that diminished absorption is associated with decreased levels of bone mass in a human infant. Such a finding contradicts the teachings of the prior art, which taught that this diminished calcium absorption had no clinical significance on bone mass accretion.

The fat blend utilized in the pediatric formula of the present invention must be low in palmitic acid, but yet contain sufficient fatty acids to support optimal infant growth and development. This may be accomplished by a blend having a fatty acid profile characterized by about 9.5–21 weight % lauric acid, about 19 weight %, or less, palmitic acid, and about 34–48 weight % oleic acid. In a further embodiment, palmitic acid content is maintained at about 15 weight %, or less, and often at about 10 weight %, or less. In an additional embodiment, the oil blend may additionally contain about 2.7–3.1 w/w % of stearic acid, about 17–29 w/w % of linoleic acid and about 1.7–3.2 w/w % of linolenic acid. A number of commercially available vegetable oils will produce this profile when blended as described in detail below.

It is believed that enhanced bone mass, continued throughout life, will make individuals less susceptible to osteoporosis when they reach their geriatric years. It is also believed infants consuming this formula will have the opportunity to achieve a greater peak bone mass.

DETAILED DESCRIPTION OF THE INVENTION

As used in this application, the following terms have the meanings defined below, unless otherwise specified. The plural and the singular should be treated as interchangeable:

1. "fatty acid profile" as used herein means the total fatty acid content of the fat, oil, emulsifiers, and other components used to create a pediatric nutritional as determined by conventional analysis. Unless specified otherwise, all percentages are weight percents of total fatty acid content. Those skilled in the art will appreciate that sometimes the levels of fatty acids are reported as grams of fatty acid, per 100 grams of fat.
2. "increasing bone mineralization" refers to the accumulation of minerals, including calcium and phosphorus, which are deposited in newly formed or remodeled bone matrix.
3. "infant" refers to a child under the age of 1 year.
4. "juvenile" refers to a child under the of age 6, and specifically includes infants, toddlers, etc.
5. Any reference to a numerical range in this application should be construed as an express disclosure of every number specifically contained within that range and of every subset of numbers contained within that range. Further, this range should be construed as providing support for a claim directed to any number, or subset of numbers in that range. For example, a disclosure of 1–10 should be construed as supporting a range of 2–8, 3–7, 5, 6, 1–9, 3.6–4.6, 3.5–9.9, 1.1–9.9, etc.
6. "pediatric formula" as used herein refers to a liquid nutritional designed for infants, toddlers, and juveniles which contains calcium, a fat blend, and optionally nutrients such as protein, vitamin, phosphorus, etc. that are required for growth and development.

The terms "bone mineralization" and "bone mass accretion" are being used interchangeably within this application. Thus within the specification or claims, they should be considered as synonyms. "Bone mineralization" should also be considered synonymous with increasing, enhancing or improving "bone strength", "bone mineral density", "bone mineral content", "bone mass", "bone accretion", etc. Likewise, the terms "palm oil" and "palm olein oil" are also being used as synonyms and should also be considered as interchangeable.

As noted above, the key to the present invention is the discovery that oil blends that inhibit the absorption of calcium produce statistically significant lower rates of bone mass accretion, when compared to oil blends which do not inhibit calcium absorption. Enhanced rates of bone mass accretion can be accomplished by limiting the quantity of palmitic acid contained within the infant formula. Based upon the overall fatty acid profile of the fat composition used in the formula, total palmitic acid content should not exceed about 19 w/w %. Such quantities of palmitic acid do not negatively impact bone mass accretion.

Limiting palmitic acid content in infant formulae goes against traditional wisdom in the field. Most infant formulae makers have attempted to utilize oil blends which create a fatty acid profile that mimics human milk. It is believed that such a profile produces superior growth and development. Palmitic acid typically makes up about 20–25 w/w % of the total fat content in human milk. A comparison of the fatty acid profile of human milk and one of the fatty acid profiles of the invention is listed below in Table I.

TABLE I

Fatty Acid Profiles of Infant Formulas, the Invention and Human Milk

| Fatty Acid weight % | Invention[1] | Human Milk* |
|---|---|---|
| 12:0 lauric | 9.5–21 | 1.4–6.5 |
| 14:0 myristic | 3.8–8.4 | 3.8–10.2 |
| 16:0 palmitic | up to about 19 | 19.8–24.0 |
| 18:0 stearic | 2.7–3.1 | 7.1–9.0 |
| 18:1n9 oleic | 34–48 | 30.7–38.0 |
| 18:2n6 linoleic | 17–29 | 5.7–17.0 |
| 18:3n3 linolenic | 1.7–3.2 | 0.1–1.8 |

1. *as reported in literature
2. [1]all quantities listed should be considered approximate and to be modified by the adjective "about", and to not specifically require the presence of all of the fatty acids listed therein, other than the express limitation upon palmitic acid content.

The fatty acid profile depicted above can be obtained with a number of vegetable oils that are routinely consumed by infants. These oils include soy, coconut, safflower, high oleic safflower(HOSO), high oleic sunflower (HOSUN), corn, medium chain triglyceride (MCT), palm kernel, palm, and palm olein. The fatty acid profile of each of these oils is listed below in Table II. One skilled in the art understands that a particular fatty acid profile can be obtained by blending different oils, based upon their individual fatty acid profiles, until the desired mix is obtained.

TABLE II

Fatty Acid Profile of Commodity Oils

| Fatty Acid weight % | Soy | Coconut | Safflower | HOSO | High Oleic Sunflower | Palm Kernel | Palm Olein | Palm | Corn | MCT |
|---|---|---|---|---|---|---|---|---|---|---|
| 6:00 caproic | — | — | — | — | — | — | — | — | — | 2.0 |
| 8:00 caprylic | — | — | — | — | — | — | — | — | — | 67.0 |
| 10:00 capric | — | — | — | — | — | — | — | — | — | 23 |
| 12:0 lauric | — | 47.1 | — | 0.1 | — | 49.6 | 0.6 | .1 | — | — |
| 14:0 myristic | 0.1 | 18.5 | 0.1 | 0.1 | — | 16 | 1.1 | 1.0 | .1 | — |
| 16:0 palmitic | 10.6 | 9.1 | 6.5 | 4.7 | 4.0 | 8.0 | 32.7 | 44.0 | 10.9 | — |
| 18:0 stearic | 4.0 | 2.8 | 2.4 | 2.2 | 4.0 | 2.4 | 3.5 | 4.1 | 2.0 | — |
| 18:1n9 oleic | 23.2 | 6.8 | 13.1 | 74.5 | 80.0 | 13.7 | 48.1 | 39.3 | 25.4 | — |
| 18:2n6 linoleic | 53.7 | 1.9 | 77.7 | 16.7 | 10.0 | 2.0 | 13.2 | 10 | 59.6 | — |
| 18:3n3 linolenic | 7.6 | 0.1 | — | 0.4 | 0.1 | — | 0.5 | .4 | 1.2 | — |

1. as reported in the literature.

The invention is not limited to the fatty acid profile depicted above in Table I. Alternative fatty acid profiles depicted below in Table III will also produce enhanced rates of bone mass accretion in infants.

TABLE III

| Fatty Acid weight % | Embodiment 1[1] | Embodiment 2[1] | Embodiment 3[1] |
|---|---|---|---|
| 12:0 lauric | 10.4–17.0 | 10.4–15.0 | 14.2 |
| 14:0 myristic | 4.2–6.7 | 4.2–6.0 | 5.6 |
| 16:0 palmitic | 7.0–8.0 | 7.5–8.0 | 7.7 |
| 18:0 stearic | 2.8–3.1 | 2.9–3.1 | 2.9 |
| 18:1n9 oleic | 37.0–45.2 | 37.6–43.0 | 40.0 |
| 18:2n6 linoleic | 21.0–28.2 | 22.0–28.0 | 22.6 |
| 18:3n3 linolenic | 2.2–3.2 | 2.3–3.2 | 2.3 |

[1]all quantities listed should be considered approximate and to be modified by the adjective "about", and to not specifically require the presence of all of the fatty acids listed therein, other than the express limitation regarding the quantity of palmitic acid.

The fatty acid profile depicted as "Embodiment 1" as set out above can be accomplished through a blend of about 3850 weight % high oleic safflower oil (HOSO/ or HOSUN), about 26–40 weight % soy oil (SO) and about 22–36 weight % coconut oil (CO).

The fatty acid profile depicted as "Embodiment 2" can be accomplished through a blend of about 41–44 weight % HOSO/HOSUN, about 27–32 weight % SO, and about 27–32 weight % CO. The fatty acid profile depicted as "Embodiment 3" can be accomplished through a blend of about 42 weight % HOSO/HOSUN, about 28 weight % SO and about 30 weight % CO.

As is readily apparent to one skilled in the art, a number of alternative oil blends will provide fatty acid profiles meeting the criteria outlined above in Tables I and ILL. Examples of such oil blends include: those containing admixtures of corn oil, high oleic safflower oil or sunflower oil, MCT oil, safflower oil and coconut oil. More specifically the benefits of the invention can be obtained with an oil blend containing about 0–60 weight % 20 of corn oil, about 20–45 weight % of coconut oil, about 25–60 weight % HOSO or HOSUN, about 0–40 weight % soy oil, about 0–40 weight % safflower oil, and about 0–35% MCT oil, with the proviso that the sum of said fatty acids does not exceed 100 weight %. Alternative blend include those containing from about 20–30 weight % coconut oil, about 45–60 weight % HOSO/HOSUN, and about 10–35% MCT oil. Other embodiments include blends containing 20–55 weight % corn oil, about 20–45 weight % of coconut oil and 25–60 weight % of HOSO/HOSUN. Numerous other variations will be readily apparent to those skilled in the art based upon the fatty acid profiles above and should be considered to be within the scope of the invention.

Other examples of suitable oil blends include: a) about 40% corn, about 20% coconut and about 40% HOSO or HOSUN; b) about 55% corn, about 20% coconut and about 25% HOSO/HOSUN; c) about 20% corn, about 45% coconut, and about 35% HOSO/HOSUN; d) about 40% coconut and about 60% HOSO/HOSUN, and; e) about 20–30% coconut, about 45–60% HOSO/HOSUN, and about 10–35% MCT. Other variations will be readily apparent to one skilled in the art.

High oleic safflower oil (HOSO) refers to oil derived from the seeds of a hybrid safflower plant, *Carthamus tinctorius*. Safflower oil is an edible oil which typically has a high content of linoleic acid. Hybrids of this plant have been developed which produce a seed oil which has an elevated level of oleic acid. It is the oil that is derived from the seeds of these hybrids which have been found useful in the present invention. Virtually interchangeable with HOSO is high oleic sunflower oil (HOSUN). Like HOSO, higholeic sunflower oil contains an elevated level of oleic acid. When used herein, the term "HOSO" includes its sunflower relative.

Soy oil (SO) refers to the fat fraction obtained from the seeds of the legume, *Soja max*. Typically, the oil fraction of the soya seed undergoes a number of refining, bleaching and deodorization steps resulting in the commercial commodity. Soy oil generally contains relatively high levels of linoleic fatty acid and to a lesser extent, linolenic fatty acid.

Coconut oil (CO) refers to the oil obtained from copra, which is dried coconut meat. This oil is distinguished from HOSO and SO by its high content of saturated, short chain and medium chain fatty acids. Palm kernel oil is very similar in fatty acid profile to CO. When used herein, the term "CO" includes its palm kernel relative.

Medium chain triglyceride oil is often referred to as "fractionated coconut oil". As its name implies, it is obtained from coconut oil. Alternatively it may be obtained from palm kernel oil. The coconut oil or palm kernel oil is submitted to chemical purification in order to enrich its relative content ofin saturated fatty acids in the $C_8$–$C_{12}$ range, especially caprylic(C:8.0) and capric(C:10.0). Techniques for carrying out such enrichments are well known to those skilled in the art.

Numerous commercial sources for the fats listed above are readily available and known to one practicing the art. For example, soy oil is available from Archer Daniels Midland of Decatur, Ill. Corn, coconut, palm and palm kernel oils are available from Premier Edible Oils Corporation of Portland, Organ. Fractionated coconut oil is available from Henkel Corporation of LaGrange, Ill. High oleic safflower and high oleic sunflower oils are available from SVO Specialty Products of Eastlake, Ohio.

In addition to the fat blend, the formula must contain calcium. Infants consuming human breast milk typically consume 250 mg to 330 mg of elemental calcium per day, with a net absorption of between 55–60%. By contrast, infants consuming formula typically consume 500 to 600 mg of elemental calcium per day. The amount of calcium that the infant absorbs is dependant upon the fat content of the formula. Calcium absorption is only about 40% if the formula contains levels of palmitic acid mimicking those of human breast milk. By contrast, the formula of this invention produce calcium absorption in the range of approximately 60%.

The infant formulae of this invention should contain from about 250 mg to about 2000 mg of elemental calcium per liter, and more typically from about 500 mg to about 1000 mg of elemental calcium per liter. Any source of calcium that is appropriate for use in a juvenile population may be utilized in the nutritionals of this invention. Examples of suitable sources of calcium include, but are not limited to, calcium carbonate, calcium chloride, calcium lactate, calcium gluconate, calcium sulfate, calcium phosphate, tricalcium phosphate, calcium citrate, tricalcium citrate, or calcium maleate.

In addition to the calcium and oil blends described above, the pediatric formula of this invention will typically contain protein, carbohydrate, vitamins, minerals, trace minerals, etc. as is known in the art. The specific sources of protein, carbohydrates, vitamins, etc., and their relative quantity, is not critical to the invention and will fit within guidelines typically used in the industry, which is described in greater detail below.

The pediatric formula of the invention may be provided in powered, liquid concentrate or ready-to-feed forms. Before feeding, water is added to both the powdered and concentrate forms of the formula. In a first embodiment, a pediatric formula of the invention comprises, based on a 100 kcal basis, about 8 to about 16 grams carbohydrate (preferably about 9.4 to about 12.3 grams), about 3 to about 6 grams fat (preferably about 4.7 to about 5.6 grams), and about 1.8 to about 3.3 grams of protein (preferably about 2.0 to about 3.3 grams). If provided in a powder form, the formula comprises, based on 100 grams of powder, about 30 to about 90 grams carbohydrate (preferably about 48 to about 59 grams), about 15 to about 30 grams fat (preferably about 22 to about 28), about 8 to about 17 grams protein (preferably about 9 to about 17 grams). A summary of the carbohydrate, fat, and protein ranges (on a per 100 kcal basis, per 100 grams powder basis and per liter basis (as fed concentration) for a formula according to the invention is provided in Table IV.

TABLE IV

RANGES OF CARBOHYDRATE, LIPID AND PROTEIN PER 100 KCAL, PER 100 GRAMS POWDER AND PER LITER (AS FED CONCENTRATION)

| Nutrient (g) | Range | Per 100 kcal | Per 100 grams powder | Per liter (as fed concentration) |
|---|---|---|---|---|
| Carbohydrate | Broadest | 8–16 | 30–90 | 53–107 |
| | Preferred | 9.4–12.3 | 48–59 | 64–83 |
| Fat | Broadest | 3–6 | 15–30 | 22–40 |
| | Preferred | 4.7–5.6 | 22–28 | 32–38 |
| Protein | Broadest | 1.8–3.3 | 8–17 | 12–22 |
| | Preferred | 2.4–3.3 | 10–17 | 14–22 |

Suitable carbohydrates, and proteins can vary widely and are well known to those skilled in the art of making pediatric formulas.

One component of the pediatric formulae is a source of carbohydrates. Carbohydrate is a major source of readily available energy that the infant needs for growth and that protects the infant from tissue catabolism. In human milk and most standard milk-based infant formulas, the carbohydrate is lactose.

The carbohydrates that may be used in the formula can vary widely. Examples of carbohydrates suitable for infants include hydrolyzed corn starch, maltodextrin, glucose polymers, sucrose, corn syrup, corn syrup solids, rice derived carbohydrate, glucose, fructose, lactose, high fructose corn syrup and indigestible oligosaccharides such as fructooligosaccharides (FOS). Any single carbohydrate listed above, or any combination thereof, as appropriate may be utilized.

Commercial sources for the carbohydrates listed above are readily available and known to one practicing the art. For example, corn syrup solids are available from Cerestar USA, Inc in Hammond, Ind. Glucose and rice based syrups are available from California Natural Products in Lathrop, Calif. Various corn syrups and high fructose corn syrups are available from Cargil in Minneapolis, Minn. Fructose is available from A. E. Staley in Decatur, Ill. Maltodextrin, glucose polymers, hydrolyzed corn starch are available from American Maize Products in Hammond, Ind. Sucrose is available from Domino Sugar Corp. in New York, N.Y. Lactose is available from Foremost in Baraboo, Wis. and indigestible oligosaccharides such as FOS are available from Golden Technologies Company of Golden, Colo.

The fats used in the formula have been described in detail above. In addition to these vegetable oils, the formula may also contain arachidonic acid, docosahexaneoic acid, and mixtures thereof. Such lipids have been shown to have beneficial effects in infants, including enhanced brain and vision development U.S. Pat. No. 5,492,938 to Kyle et al. describes these effects in greater detail. Lipid sources of arachidonic acid and docosahexaneoic acid include, but are not limited to, marine oil, egg derived oils, and fungal oil. Marine oil is available from Mochida International of Tokyo, Japan. DHA is available from Martek Biosciences Corporation of Columbia, Md. Arachidonic acid is available from Genzyme Corporation of Cambridge, Mass.

The proteins that may be utilized in the pediatric formula of the invention include any proteins or nitrogen source suitable for human consumption. Such proteins are well known by those skilled in the art and can be readily selected when preparing such products. Examples of suitable protein sources include casein, whey, condensed skim milk, nonfat milk, soy, pea, rice, corn, hydrolyzed protein, free amino acids, and mixtures thereof.

Commercial protein sources are readily available and known to one practicing the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of Saint Louis, Missouri. Pea protein is available from Feinkost Ingredients Company of Lodi, Ohio. Rice protein is available from California Natural Products of Lathrop, Calif. Corn protein is available from EnerGenetics Inc. of Keokuk, Iowa. Additionally, mineral enriched proteins are available from New Zealand Milk Products of Santa Rosa, Calif. and Protein Technologies International of Saint Louis, Miss.

A formula of the invention preferably also contains vitamins and minerals in an amount designed to supply the daily nutritional requirements of a pediatric population. The formula preferably includes, but is not limited to, the following vitamins and minerals: phosphorus, sodium, chloride, magnesium, manganese, iron, copper, zinc, selenium, iodine, and Vitamins A, E, C, D, K and the B complex. Further nutritional guidelines for infant formulas can be found in the Infant Formula Act, 21 U.S.C. section 350(a). The nutritional guidelines found in the Infant Formula Act continue to be refined as further research concerning infant nutritional requirements is completed. This invention is intended to encompass formulas containing vitamins and minerals that may not currently be listed in the Act.

The pediatric formulas of this invention can be manufactured using techniques well known to those skilled in the art. Various processing techniques exist for producing powdered, ready-to-feed and concentrate liquid formulas. Typically, these techniques include formation of a slurry from one or more solutions which may contain water and one or more of the following: carbohydrates, proteins, lipids, stabilizers, vitamins and minerals. This slurry is emulsified, homogenized and cooled. Various other solutions may be added to the slurry before processing, after processing or at both times. The processed formula is then sterilized and may be diluted to be utilized on a ready-to-feed basis or stored in a concentrated liquid or a powder. If the resulting formula is meant to be a ready-to-feed liquid or concentrated liquid, an appropriate amount of water would be added before sterilization. If the resulting formula is meant to be a powder, the slurry will be heated and dried to obtain a powder. The powder resulting from drying may be dry blended with further ingredients, if desired.

In actual use, the formula of this invention may be consumed by any human. More specifically, the specified fat composition of this invention may be incorporated into a formula which is in compliance with accepted levels of vitamins, minerals, micro-components and the like. The amount consumed does not differ from that associated with the normal consumption of commercially available infant formula. The caloric density (i.e., kcals/ml) and caloric distribution (i.e., the relative proportion of calories from fat, protein and carbohydrate) are not critical to this invention but are generally comparable to conventional formulas. As is well know to those skilled in the art, these factors can vary with the intended use of the formula. For example, preterm, term and toddler infants have somewhat differing caloric density requirements. Also, formulas for specific disease states (e.g., diabetes, pulmonary deficiency, in-born errors of metabolism, and immune comprised) will have differing caloric distributions. Those skilled in the art are aware of these differences and will readily adapt the present invention to meetthose special needs.

The invention has been described as a method of enhancing the bone mass of infants, juveniles, children, etc. It should be understood that any human being, regardless of their age, will experience enhanced calcium absorption, with the fat blends of this invention. As a practical matter however, typically only infants and toddlers consume such formula. The invention should be construed as covering any human being who consumes the nutritionals described above.

The following examples are illustrative of the methods and compositions of the invention for enhancing bone mass growth in pediatric patients. While the invention is described in terms of a ready-to-feed infant nutritional formula in the examples, below, it is not intended to be so limited, as it is intended to encompass both powdered and concentrate liquid infant formulas as well as formulas for children one year in age or older. The examples are not intended to be limiting as other carbohydrates, lipids, proteins, stabilizers, vitamins and minerals may be used without departing from the scope of the invention.

EXAMPLE I

The following Example illustrates the preparation of a ready-to-feed infant formula suitable for carrying out the method of the present invention. The components utilized in the formula are depicted Table V. The quantities outlined were used to preparea 7711 Kg batch of formula.

TABLE V

| INGREDIENT | AMOUNT |
| --- | --- |
| High Oleic Safflower Oil | 120.2 Kg |
| Coconut Oil | 85.7 Kg |
| Soy Oil | 80.3 Kg |
| Lecithin | 2.92 Kg |
| Mono- and diglyceride | 2.92 Kg |
| Oil Soluble Vit, Premix | 0.365 Kg |
| -carotene | 0.0137 Kg |
| Carrageenan | 1.43 Kg |
| Whey Protein Concentrate | 61.2 Kg |
| Lactose | 476.3 Kg |
| Potassium Citrate | 4.6 Kg |
| Magnesium Chloride | 0.735 Kg |
| Low Heat Condensed Skim Milk | 821 Kg |
| Calcium Carbonate | 3.36 Kg |
| Ferrous sulfate | 0.450 Kg |
| Water Soluble Vitamin Premix | 1.11 Kg |
| Trace Minerals/Taurine | |
| Choline Chloride | 0.600 Kg |
| Adenosine 5' monophosphate | 0.113 Kg |
| Guanosine 5' monophosphate-Na2 | 0.197 Kg |
| Cytidine 5' monophosphate | 0.259 Kg |
| Uridine 5' monophosphate-Na2 | 0.216 Kg |
| Ascorbic Acid | 1.78 Kg |
| 45% KOH | 2.36 Kg |
| Total Yield | 7711 Kg |

The first step in the preparation of formulas is the preparation of the oil blend. To an appropriately sized blend tank with agitation and heating soy oil, coconut oil and high oleic safflower oil were added. The mixture was heated to 73.8–79.4° C. The lecithin and mono-and diglycerides (Myverol 18- 06) were added to the blend tank with agitation. The oil soluble vitamin premix was added with agitation. The premix container was rinsed with the oil blend and transferred back to the blend tank to ensure complete delivery of the vitamin premix. The β-carotene was added to the oil blend and the mixture agitated until the components were well dispersed. The β-carotene container was rinsed with the oil blend and the contents returned to the blend tank to ensure complete delivery of the carotene solution. Lastly, the carrageenan was added to the oil blend and the mixture was agitated and held at 54.0–60° C. until used.

The carbohydrate, mineral and CSM (condensed skim milk) protein slurry was prepared next. To water heated to 68–73° C. the lactose was added and the mixture agitated until the lactose was well dissolved. Potassium citrate was then added followed by potassium chloride, sodium chloride and magnesium chloride. The condensed skim milk (CSM) and tricalcium phosphate were then added and the mixture was agitated and held at 54–60° C. until used.

The protein-in-water (PIW) slurry was then prepared. The whey protein concentrate was added to water at 54–60° C. under mild agitation. The PIW slurry was held under mild agitation until needed. Also contemplated in this invention is the use of protein-in-fat (PIF) slurries, wherein an appropriate amount of protein is admixed with all or a portion of the oil (fat) component.

The PIW slurry was then added to the prepared oil blend. The required amount of the carbohydrate, mineral and CSM slurry was then added to the oil blend. The pH of the mixture was then determined and if below specification, it was adjusted using KOH to a pH of 6.75 to 6.85. The mixture was then held at 5460° C. under agitation for at least 15 minutes.

The mixture was then heated to 68–74° C. and deaerated under vacuum. The mixture was then emulsified through a single stage homogenizer at 6.21 to 7.58 MPa. After emulsification, the mixture was heated to 120–122° C. for 10 seconds and then 149–150° C. for 5 seconds. The mixture was then passed through a flash cooler to reduce the temperature to 120–122° C. and then through a plate cooler to reduce the temperature to 71–79° C. The mixture was then passed through a two stage homogenizer at 26.89 to 28.27 MPa and 2.76 to 4.14 MPa. The mixture was held at 73 to 83° C. for 16 seconds and then cooled to 1 to 7° C. At this point, samples are taken for microbiological and analytical testing. The mixture was held under agitation.

A calcium carbonate solution may be prepared for use in adjusting the calcium level of the mixture if outside of specification.

A vitamin stock solution was prepared. To water heated at 37 to 66° C. was added potassium citrate and ferrous sulfate. The vitamin premix was then added and the mixture agitated. The choline chloride was added and then the required amount of this vitamin mixture was added to the batch.

The nucleotide solution was then prepared. The following nucleotides were added to water with mild agitation in the following order: AMP, GMP, CMP, UMP. Agitation was continued for about 10 minutes to dissolve the nucleotides. The nucleotide solution was then added to the batch.

Lastly, an ascorbic acid solution was prepared and added slowly to the batch with agitation for at least 10 minutes. Final dilution with water to meet specified levels of solids and caloric density was completed. The batch was then packaged in 0.9 Kg (32 ounce) metal cans and sterilized using conventional technology.

EXAMPLE II

Human Clinical Study

The study was undertaken to demonstrate that the reduced absorption of calcium does have clinical significance, despite the contrary teachings of the prior art. Two formula's that differed primarily based upon their palmitic acid content were evaluated in the study.

The study design was a controlled, masked (for investigator and subjects), randomized, parallel 6-month feeding in healthy, term infants comparing bone mineralization between two study formula groups.

The two study formulas were (1) a milk-based formula with palm-olein as a predominant oil, MFP (prior art) (Enfamil With Iron, Mead Johnson, Evansville, Ind.), and (2), a milk-based formula with no palm-olein, MF (invention) (Similac With Iron, Ross Products, Columbus, Ohio). Both study formulas were ready-to-feed (RTF) and contained cow's milk protein. They both provided 20 kcal per fl oz, and were packaged in clinically labeled 32 fl oz cans for masking or blinding purpose. The two formulas are commercially available and meet or exceed the levels of nutrients recommended by the American Academy of Pediatrics Committee on Nutrition (AAP-CON)[4] and the Infant Formula Act of 1980 and subsequent amendments. Nutrient compositions of the 2 study formulas are presented in Table VI. The nutrient composition are generally comparable except for the fat blend. The MF had a fat blend of 42% high-oleic safflower, 30% coconut, and 28% soy oils. In contrast, the MFP had a fat blend of 45% palm-olein, 20% coconut, 20% soy, and 15% high-oleic safflower oils. As a result, the palmitic acid levels in MF and MFP were about 8.2% and 22.1%, respectively.

Methods:

The study Procedures and Assessments involved identifying and enrolling subjects, obtaining written informed consents, and randomization into one of two formula groups and fed for 6 months. Total body bone mineral content (BMC) and density (BMD) were determined at enrollment time and at 12 and 26 weeks of age, using dual-energy x-ray absorptiometry (QDR, DXA instruments, Hologic Inc, Waltham, Mass.). Bone scans were done with Models QDR 2000 and/or 4500A using a standard procedure.[5] BMC was the primary outcome variable in the study. Weight, length, and head circumference were measured at enrollment and at 4, 12, and 26 weeks of age. Formula intake and frequency of feeding (number of feedings) by subjects were determined by recording dietary intake on appropriate intake forms. The forms were filled out by parents for 3 consecutive days prior to scheduled study visits at 4, 12, and 26 weeks of age. Total occurrence of serious or unexpected adverse events (SAEs) and the relationship of SAEs to study products were assessed and used to evaluate safety in this study. The study was approved by the ethic committee/institutional review board of the study research center (Wayne State University, Hutzel Hospital, Detroit, Mich.)

Key Statistical comparisons for this study focused on total body bone mineral content (BMC) as the primary outcome variable of interest. Statistical tests of hypotheses were two-tailed; p-values less than 0.05 were considered statistically significant. Analyses were reported on an "intent-to-treat" basis, i.e. including all available data on all randomized infants. Infants who discontinued study feeding were asked to return for DXA scan measurements at the projected 3 month and 6 month visits. A confirmatory analysis was done on BMC, BMD, weight, length, head circumference, average number of feedings per day and average volume (in mls) of study formula fed per day on those infants who were fed the assigned study formula throughout the 6 month feeding period as required by the protocol. BMC, BMD, weight, length, and head circumference were analyzed using repeated measures analysis. With repeated measured analysis, comparison of study feedings at 3 months only were made using an ANOVA test if there was no significant feeding*visit interactions. Comparisons at both 3 and 6 months were made if feeding*visit interactions were significant. Weight at scan time and type of DXA scanner machine were included as a covariate for the analysis of BMC and BMD in this study. Birth weight, birth length and birth head circumference were included as covariates for their corresponding analysis of anthropometrics in this study. Ethnicity was included as a blocking factor in the analysis of variance for exit information continuous variables. For exit information categorical variables, ethnicity was incorporated into tests of association using Cochran-Mantel-Haenszel tests. All analyses were done using either SAS Release 6.09e or PC SAS Release 8.0.

TABLE VI

Composition of Clinical Study Formulas (Per Liter)

| Nutrient | MF (invention) | MFP (prior art) |
|---|---|---|
| Protein, g | 14 | 14.2 |
| Source | nonfat milk, whey protein concentrate | reduced minerals whey, nonfat milk |
| Fat, g | 36.5 | 35.8 |
| Source | High-oleic safflower (42%), coconut (30%), & soy (28%) oils | palm olein (45%), coconut (20%), soy (20%), & high-oleic sunflower (15%) oils |
| Carbohydrate, g | 73.0 | 73.7 |
| Source | lactose | lactose |
| Linoleic acid, g | 7.4 | 5.8 |
| Minerals | | |
| Calcium, mg | 527 | 527 |
| Phosphorous, mg | 284 | 358 |
| Magnesium, mg | 40.6 | 54.1 |
| Iron, mg | 12.2 | 12.2 |
| Zinc, mg | 5.1 | 6.8 |
| Manganese, $\mu$g | 33.8 | 101 |
| Copper, mg | 0.61 | 0.51 |
| Iodine, $\mu$g | 40.6 | 67.6 |
| Sodium, mg | 162 | 183 |
| Potassium, mg | 710 | 730 |
| Chloride, mg | 433 | 426 |
| Selenium, $\mu$g | 14 | 18.9 |
| Vitamins | | |
| A, IU | 2028 | 2028 |
| D, IU | 406 | 406 |
| E, IU | 20.3 | 13.5 |
| $K_1$, $\mu$g | 54.1 | 54.1 |
| C, mg | 60.8 | 81.1 |
| Thiamine ($B_1$), $\mu$g | 676 | 541 |
| Riboflavin ($B_2$), $\mu$g | 1014 | 946 |
| $B_6$, $\mu$g | 406 | 406 |
| $B_{12}$, $\mu$g | 1.7 | 2.03 |
| Niacin, $\mu$g | 7098 | 6760 |
| Folic acid, $\mu$g | 101 | 108 |
| Pantothenic acid, $\mu$g | 3042 | 3380 |
| Biotin, $\mu$g | 29.7 | 20.3 |
| Choline, mg | 108 | 81.1 |
| m-Inositol, mg | 31.8 | 40.6 |
| $\beta$-carotene, $\mu$g | 400 | — |

Values are label claim

Results:

Infants enrolled into this study were healthy, singleton and full term by birth (gestational age of 37 to 42 weeks). All subjects enrolled in the study had written informed consent forms voluntarily signed and dated by a parent or guardian. One hundred twenty-eight (128) infants were randomized and enrolled into this study; 102 infants completed the study through 6 months (79.7%); 26 infants (20.3%) discontinued the study post-randomization. Fifteen (15) infants (23%) in the MF feeding group and 10 infants (16%) in the MFP feeding group withdrew from the study by the 3 month visit and an additional infant (18205) in the MFP feeding group withdrew from the study by the 6 month visit. There were no significant differences between the feeding groups with respect to gender, ethnicity or study completion or withdrawal rate. The distribution of infants is summarized by gender, ethnicity and study termination Table VII.

TABLE VII

Demographics and Study Exit Status of Enrolled Subjects

| | Feeding Group | | | |
|---|---|---|---|---|
| | MF (invention) (n = 65) | MFP (prior art) (n = 63) | Total (N = 128) | p-value |
| Sex | | | | |
| Male, n (%) | 30 (46.2) | 27 (42.9) | 57 (44.5) | 0.726[1] |
| Female, n (%) | 35 (53.9) | 36 (57.1) | 71 (55.5) | |
| Ethnicity | | | | |
| Black, n (%) | 36 (55.4) | 36 (57.1) | 72 (56.3) | 0.860[1] |
| Non-Black, n (%) | 29 (44.6) | 27 (42.9) | 56 (43.8) | |
| White | 24 | 24 | 48 | |
| Hispanic | 3 | 2 | 5 | |
| Asian | 1 | 0 | 1 | |
| Other | 1 | 1 | 2 | |
| Study Termination | | | | |
| Withdrew from the Protocol, n (%) | 15 (23.1) | 11 (17.5) | 26 (20.3) | 0.398[2] |
| <3 months | 15 | 10 | 25 | |
| 3 < 6 months | 0 | 1 | 1 | |
| Completed Study According to Protocol or with Acceptable Variations, n (%) | 50 (76.9) | 52 (82.5) | 102 (79.7) | |

[1]Fisher's Exact Test
[2]Cochran-Mantel-Haenszel Test Controlling for Ethnicity-General Association There were no significant differences between the feeding groups with respect to age at study day 1, birth head circumference, maternal age and gestational age. (Table VIII)

TABLE VIII

Baseline Measurements (Age at Study Day 1, Birth Weight, Birth Length, Birth Head Circumference, Gestational Age)

| | Feeding Group | | |
|---|---|---|---|
| | MF (invention) | MFP (prior art) | p-value |
| Age at study day 1, days | 5.6 ± 0.5 (65) | 6.3 ± 0.5 (63) | ns |
| Birth weight, g | 3372 ± 42 (64) | 3329 ± 42 (63) | ns |
| Birth length, cm | 50.9 ± 0.3 (64) | 50.5 ± 0.3 (62) | ns |
| Birth head circumference, cm | 34.0 ± 0.2 (64) | 34.0 ± 0.2 (61) | ns |
| Maternal Age, years | 25.7 ± 0.7 (65) | 25.3 ± 0.7 (63) | ns |
| Gestational Age, months | 39.4 ± 0.2 (65) | 39.4 ± 0.2 (63) | ns |

Values are Means ± SEM (N).

Primary Outcome Variable

For the adjusted analysis of the intent-to-treat population in which types of DXA instrument use were controlled for, BMC was significantly higher in infants fed MF compared to infants fed MFP at both 3 months (p=0.012) and 6 months (p=0.032). For the adjusted analysis of the evaluable subgroup, BMC was significantly higher in infants fed MF compared to infants fed MFP over the 6 month period (p=0.002) and also at 3 months only (p=0.004). For the unadjusted analysis of the intent-to-treat population, there was not a significant difference between MF and MFP for BMC over the 6 month period (p=0.056), however BMC was significantly higher in infants fed MF compared to infants fed MFP at 3 months only (p=0.015). For the unadjusted analysis of the evaluable subgroup, BMC was significantly higher in infants fed MF compared to infants fed MFP over the 6 month period (p=0.015) and at 3 months only (p=0.019). As seen in the results in Table IX, BMC was significantly higher for infants fed MF than for infants fed MFP at 3 months with the difference still present, although lessened, at 6 months for the intent-to-treat population. BMC was significantly higher for infants fed MF than for infants fed MFP over the entire 6 month period and at all visits for the evaluable subgroup.

TABLE IX

Bone Mineral Content (g)

| Feeding Group | | p-value (un-adjusted) | p-value (adjusted for machine) |
|---|---|---|---|
| MF (invention) | MFP (prior art) | | |
| Intent-to-Treat Population | | 0.056[1, #] | $ |
| Enroll-ment | 59.5 ± 1.2 (64) | 59.1 ± 1.3 (63) | | 0.958[2] |
| 3 months | 105.6 ± 2.7 (50) | 96.1 ± 2.2 (53) | 0.015[3] | 0.012[2] |
| 6 months | 149.7 ± 3.7 (50) | 139.3 ± 3.0 (52) | | 0.032[2] |
| Evaluable Subgroup | | | 0.015[1, @] | 0.002[1, &] |
| Enroll-ment | 60.2 ± 1.3 (48) | 57.9 ± 1.4 (51) | | |
| 3 months | 105.2 ± 2.8 (48) | 96.0 ± 2.3 (51) | 0.019[3] | 0.004[3] |
| 6 months | 149.1 ± 3.7 (48) | 139.1 ± 3.0 (51) | | |

Values are Means ± SEM (N).
[#]Feeding Group*Visit interaction not significant (p = 0.085) -> Feeding Group effect tested at 3 months only
[$]Feeding Group*Visit interaction significant (p = 0.037) -> Feeding Group effect tested by Visit
[@]Feeding Group*Visit interaction not significant (p = 0.101) -> Feeding Group effect also tested at 3 months only
[&]Feeding Group*Visit interaction not significant (p = 0.101) -> Feeding Group effect also tested at 3 months only
[1]Repeated measures ANOVA Type 3 Test of Feeding Group Fixed Effect (over all visits)
[2]Repeated measures ANOVA Type 3 Test of Feeding Group*Visit Effect Slice-by Visit
[3]ANOVA Type 3 Test of Feeding Group Effect at 3 months only Secondary Variables Bone Mineral Density (BMD) (g/cm$^2$)

For the adjusted analysis of the intent-to-treat population, BMD was significantly higher in infants fed MF compared to infants fed MFP at 3 months (p=0.004) and at 6 months (p=0.0498) as seen in Table X. For the adjusted analysis of the evaluable subgroup, BMD was significantly higher in infants fed MF compared to infants fed MFP over the 6 month period (p<0.001) and also at 3 months only (p<0.001). For the unadjusted analysis of the intent-to-treat population, BMD was significantly higher in infants fed MF compared to infants fed MFP at 3 months (p=0.008). For the unadjusted analysis of the evaluable subgroup, BMD was significantly higher in infants fed MF compared to infants fed MFP over the 6 month period (p=0.007) and at 3 months only (p=0.003).

TABLE X

Bone Mineral Density (g/cm$^2$)

| Feeding Group | | p-value (un-adjusted) | p-value (adjusted for machine) |
|---|---|---|---|
| MF | MFP | | |
| Intent-to-Treat Population | | # | $ |
| Enroll-ment | 0.203 ± 0.002 (64) | 0.203 ± 0.002 (63) | 0.999[2] | 0.865[2] |
| 3 months | 0.230 ± 0.003 (50) | 0.216 ± 0.003 (53) | 0.008[2] | 0.004[2] |
| 6 months | 0.262 ± 0.004 (50) | 0.249 ± 0.003 (52) | 0.097[2] | 0.0498[2] |
| Evaluable Subgroup | | 0.007[1, @] | <0.001[1, &] |
| Enroll-ment | 0.205 ± 0.003 (48) | 0.201 ± 0.003 (51) | | |
| 3 months | 0.230 ± 0.003 (48) | 0.216 ± 0.003 (51) | 0.003[3] | <0.001[3] |
| 6 months | 0.261 ± 0.004 (48) | 0.249 ± 0.003 (51) | | |

Values are Means ± SEM (N).
[#]Feeding Group*Visit interaction significant (p = 0.031) -> Feeding Group effect tested by Visit
[$]Feeding Group*Visit interaction significant (p = 0.019) -> Feeding Group effect tested by Visit
[@]Feeding Group*Visit interaction not significant (p = 0.105) -> Feeding Group effect also tested at 3 months only
[&]Feeding Group*Visit interaction not significant (p = 0.104) -> Feeding Group effect also tested at 3 months only
[1]Repeated measures ANOVA Type 3 Test of Feeding Group Fixed Effect (over all visits)
[2]Repeated measures ANOVA Type 3 Test of Feeding Group*Visit Effect Slice-by Visit
[3]ANOVA Type 3 Test of Feeding Group Effect at 3 months only Anthropometrics There was no significant difference between feeding groups with respect to weight, length, and head circumference over the course of this study. However, MF was found to be higher than MFP in Males only. (Table XI).

TABLES XI

Weight, Length, and Head Circumference Measures of Study Subjects From Enrollment to 26 Weeks of Age.

| Variable | MF | MFP | p-Value |
|---|---|---|---|
| Weight, g | | | |
| Enrollment | 3357 ± 47 (65) | 3363 ± 45 (63) | ns |
| Week 4 | 4314 ± 61 (53) | 4130 ± 49 (55) | ns |
| Week 12 | 5911 ± 97 (50) | 5730 ± 79 (53) | ns |
| Week 26 | 7787 ± 138 (50) | 7602 ± 100 (52) | ns |
| Length, cm | | | |
| Enrollment | 48.8 ± 0.3 (65) | 48.6 ± 0.2 (63) | ns |
| Week 4 | 52.6 ± 0.3 (53) | 51.6 ± 0.2 (55) | ns |
| Week 12 | 58.7 ± 0.3 (50) | 57.8 ± 0.2 (53) | ns |
| Week 26 | 66.0 ± 0.3 (50) | 65.5 ± 0.3 (52) | ns |
| Head Circumference, cm | | | |
| Enrollment | 34.8 ± 0.2 (65) | 34.9 ± 0.1 (63) | ns |
| Week 4 | 37.4 ± 0.2 (53) | 37.1 ± 0.1 (55) | ns |
| Week 12 | 40.3 ± 0.2 (50) | 40.1 ± 0.1 (53) | ns |
| Week 26 | 43.4 ± 0.2 (50) | 43.3 ± 0.2 (52) | ns |

Values are mean ± SEM (n).

Volume of Intake (Avg Volume (mls) of Study Formula Fed/Day)

For the intent-to-treat population, formula intake was similar throughout the study except at 4 weeks and 6 weeks.

Intake was significantly higher for infants fed MF compared to infants fed MFP at 4 weeks (p=0.037), while formula intake was significantly higher for infants fed MFP compared to infants fed MF at 26 weeks (p=0.043), Frequency of food intake was not different between the 2 formula groups. (Table XII).

TABLE XII

Volume of Intake (Avg mls Study Formula Fed/day)-Intent-to-Treat Population

| | Feeding Group | | |
|---|---|---|---|
| | MF | MFP | p-value |
| | | | # $ |
| Week 3 | 832 ± 47 (51) | 744 ± 23 (51) | 0.056[1] |
| Week 4 | 913 ± 56 (51) | 795 ± 23 (53) | 0.037[1] |
| Week 8 | 972 ± 31 (45) | 1025 ± 35 (51) | 0.310[1] |
| Week 12 (Month 3) | 1072 ± 41 (47) | 1109 ± 41 (51) | 0.396[1] |
| Week 16 | 1152 ± 51 (49) | 1210 ± 44 (46) | 0.388[1] |
| Week 21 | 1181 ± 47 (49) | 1235 ± 49 (47) | 0.488[1] |
| Week 26 (Month 6) | 1097 ± 58 (50) | 1238 ± 49 (46) | 0.043[1] |

Values are Means ± SEM (N)
Feeding Group*Gender interaction not significant (p = 0.701) -> Feeding Group effect not tested by Gender
$Feeding Group*Visit interaction significant (p = 0.020) -> Feeding Group effect tested by Visit
[1]Repeated measures ANOVA Type 3 Test of Feeding Group*Visit Effect Slice-by Visit Serious and/or Unexpected Adverse Events (SAE's)

The number of infants who had a Serious and/or Unexpected Adverse Event (SAE) and the total number of SAEs were compared by feeding group. There were no significant differences between feeding groups for either the number of infants who had an SAE of the total number of SAEs. There were 2 subjects in the MF group and 5 subjects with recorded SAEs during this study; and none were life threatening.

Conclusions

This study clearly demonstrates that high levels of palmitic acid not only diminish calcium absorption, but that they also lead to decreased bone mineralization and decreased bone mass in the infant. Formula that does not attempt to mimic the fatty acid profile of human milk leads to enhanced rates of bone mineralization.

REFERENCES

1. Nelson S E, Frantz J A, Ziegler E E: Absorption of fat and calcium by infants fed a milk-based formula containing palm-olein *J Am Coll Nutr* 1998;17:327–332.
2. Nelson S E, Rogers R R, Frantz J A, Ziegler E E: Palm olein in infant formula: Absorption of fat and minerals by normal infants. *J Am Clin Nutr* 1996;64:291–296.
3. Specker B L, Beck A, Kalkwarf H, Ho M: Randomized trial of varying mineral intake on total body bone mineral accretion during the first year of life. *Pediatrics* 1997;99 (6):e12
4. American Academy of Pediatrics Committee on Nutrition:*Pediatric Nutrition Handbook* Elk Grove Village, Ill.: American Academy of Pediatrics, 1993, pp 190, 360–361.
5. Koo W K, Bush A J, Walters J, Carlson S E: Postnatal development of bone mineral status during infancy. *J Am Coll Nutr* 1998; 17:65–70.

We claim:

1. A method for increasing bone mineralization in a juvenile comprising enterally feeding said juvenile a formula containing a source of calcium and a source of fat, in which the fatty acid profile of said fat contains at most about 19 weight % of palmitic acid.

2. The method according to claim 1 wherein said human is an infant or toddler.

3. The method according to claim 2 in which said fat contains at most about 15 weight % of palmitic acid.

4. The method according to claim 2 in which said fat has the following fatty acid profile:

a) about 9.5–21 weight % lauric acid;
   b) up to about 15 weight % palmitic acid, and;
   c) about 34–48 weight % oleic acid.

5. The method according to claim 2 in which said fat has the following fatty acid profile:

a) about 9.5–21 weight % lauric acid;
   b) up to about 10 weight % palmitic acid, and;
   c) about 34–48 weight % oleic acid.

6. The method according to claim 2 in which said fat has the following fatty acid profile:

a) about 10.4–17.1 weight % lauric acid;
   b) about 7.0–8.0 weight % palmitic acid; and
   c) about 37.0–45.2 weight % oleic acid.

7. A method for increasing bone mineralization in a juvenile comprising enterally feeding said juvenile a formula containing a source of calcium and a source of fat, in which said fat comprises, based on the weight of the total fat:

a) about 35–55 weight % high oleic safflower oil or high oleic sunflower oil;
   b) about 20–40 weight % soy oil; and
   c) about 20–45 weight % coconut oil.

8. The method according to claim 7 in which said human is an infant or toddler.

9. A method for enhancing bone mass accretion comprising administering to a toddler or infant a formula containing a source of calcium and a source of fat, in which said fat comprises, based on the weight of the total fat:

a) from about 0 to about 56 weight % of corn oil;
   b) from about 25 to about 60 weight % of high oleic safflower oil, or high oleic sunflower oil;
   c) from about 20 to about 45 weight % of coconut oil, and;
   d) about 0–40 weight % soy oil;
   e) about 0–40 weight % safflower oil, with the proviso that the total weight % of oil does not exceed 100;
   f) from about 0 to about 35 weight % of MCT oil.

* * * * *